United States Patent
Wang et al.

(10) Patent No.: US 11,892,442 B2
(45) Date of Patent: Feb. 6, 2024

(54) COMPREHENSIVE SYSTEM FOR POTENTIAL RISK IDENTIFICATION AND POLLUTION PREWARNING OF GROUNDWATER

(71) Applicant: Technical Centre for Soil, Agriculture and Rural Ecology and Environment, MEE, Beijing (CN)

(72) Inventors: Yu Wang, Beijing (CN); Chunsheng Lv, Beijing (CN); Qijia Lou, Beijing (CN); Quanli Liu, Beijing (CN); Kuo Tang, Beijing (CN); Danqing Liu, Beijing (CN); Zhenyu Zhong, Beijing (CN); Xueting Shao, Beijing (CN); Jing Li, Beijing (CN); Dongdong Wang, Beijing (CN); Ke Li, Beijing (CN); Wei Wang, Beijing (CN); Zengguang Yan, Beijing (CN); Guanlin Guo, Beijing (CN); Hao Wu, Beijing (CN)

(73) Assignee: Technical Centre for Soil, Agriculture and Rural Ecology and Environment, Ministry of Ecology and Environment, Beijing (CN)

( * ) Notice: Subject to any disclaimer, the term of this patent is extended or adjusted under 35 U.S.C. 154(b) by 0 days.

(21) Appl. No.: 18/098,119

(22) Filed: Jan. 18, 2023

(65) Prior Publication Data

US 2023/0236163 A1    Jul. 27, 2023

(30) Foreign Application Priority Data

Jan. 25, 2022    (CN) .......................... 202210085529.2

(51) Int. Cl.
*G01N 33/18*    (2006.01)

(52) U.S. Cl.
CPC .................................... *G01N 33/18* (2013.01)

(58) Field of Classification Search
CPC ............................... G01N 33/18; G01N 1/405
See application file for complete search history.

(56) References Cited

U.S. PATENT DOCUMENTS

| 4,042,497 A | * | 8/1977 | Maltby | .................... C02F 3/046 |
| | | | | 210/744 |
| 4,886,088 A | * | 12/1989 | Ryokai | .................... B05B 12/12 |
| | | | | 239/63 |

(Continued)

FOREIGN PATENT DOCUMENTS

| CN | 103033540 B | * | 1/2015 | |
| CN | 112223964 A | * | 1/2021 | ............ B60F 3/0015 |

(Continued)

*Primary Examiner* — David A. Rogers
(74) *Attorney, Agent, or Firm* — Bayramoglu Law Offices LLC

(57) ABSTRACT

A comprehensive system for potential risk identification and pollution prewarning of groundwater comprises a cable laying device, a monitoring cable, and an electromagnetic retrieving device which are located in groundwater between two adjacent wells, wherein the two adjacent wells comprise a first well and a second well, the second well is located at a lower water level of the first well and communicates with the first well, the electromagnetic retrieving device is located in the second well, a plurality of sensors are arranged on the monitoring cable, and one end of the monitoring cable is connected to the cable laying device. The cable laying device comprises a device body, an anchoring module arranged at a bottom of the device body, and an electromagnetic adsorption module arranged on the device body. The monitoring cable is connected to the cable laying device after passing through the anchoring module.

4 Claims, 4 Drawing Sheets

(56) References Cited

U.S. PATENT DOCUMENTS

| | | | | |
|---|---|---|---|---|
| 4,986,905 A * | 1/1991 | White | ............... | C02F 3/046 405/51 |
| 5,155,356 A * | 10/1992 | Peters | ............... | G01M 3/005 250/392 |
| 5,252,000 A * | 10/1993 | Mohs | ............... | E21B 43/121 210/170.07 |
| 5,497,091 A * | 3/1996 | Bratton | ............... | G01V 3/02 324/438 |
| 5,676,828 A * | 10/1997 | Kallenbach | ............... | C02F 3/10 210/260 |
| 5,942,440 A * | 8/1999 | Dooley | ............... | G01N 33/1826 436/139 |
| 6,016,714 A * | 1/2000 | Smith | ............... | E02F 5/145 73/866.5 |
| 6,021,664 A * | 2/2000 | Granato | ............... | E21B 49/084 210/170.07 |
| 6,491,828 B1 * | 12/2002 | Sivavec | ............... | G01N 33/18 210/170.07 |
| 6,530,263 B1 * | 3/2003 | Chana | ............... | G01M 3/243 73/40.5 R |
| 6,734,674 B1 * | 5/2004 | Struse | ............... | G01V 3/12 324/693 |
| 6,938,461 B1 * | 9/2005 | Johnson | ............... | E21B 49/00 73/37 |
| 6,948,882 B2 * | 9/2005 | Smith | ............... | G21F 9/34 588/249 |
| 6,978,794 B2 * | 12/2005 | Dukes | ............... | A01G 25/167 239/69 |
| 7,003,405 B1 * | 2/2006 | Ho | ............... | G01V 9/007 702/9 |
| 7,156,581 B2 * | 1/2007 | Zomer | ............... | B09C 1/002 405/128.7 |
| 7,229,593 B1 * | 6/2007 | Ho | ............... | G01N 13/00 73/1.01 |
| 7,788,970 B2 * | 9/2010 | Hitt | ............... | A01G 25/167 73/73 |
| 8,215,164 B1 * | 7/2012 | Hussain | ............... | E21B 47/10 73/152.33 |
| 8,340,927 B2 * | 12/2012 | Sung | ............... | G01F 1/007 702/50 |
| 8,765,060 B2 * | 7/2014 | Buhlmann | ............... | G01N 27/3335 436/68 |
| 9,709,471 B2 * | 7/2017 | Riess | ............... | G01N 1/02 |
| 10,386,261 B2 * | 8/2019 | Al-Sayed Wahba | ............... | F17D 5/06 |
| 10,480,803 B2 * | 11/2019 | Hatton | ............... | F24F 11/52 |
| 10,560,764 B2 * | 2/2020 | Solomon | ............... | H04Q 9/04 |
| 10,738,603 B2 * | 8/2020 | Heller | ............... | E21B 49/084 |
| 10,852,209 B2 * | 12/2020 | Mine | ............... | G01M 3/243 |
| 11,048,279 B2 * | 6/2021 | Samburg | ............... | G05D 9/12 |
| 11,150,166 B2 * | 10/2021 | Hou | ............... | G01N 1/10 |
| 11,435,252 B2 * | 9/2022 | Challener | ............... | G01M 3/22 |
| 11,519,809 B2 * | 12/2022 | Ziolkowski | ............... | G01M 3/20 |
| 2011/0003400 A1 * | 1/2011 | Halden | ............... | G01N 1/405 422/430 |
| 2016/0033462 A1 * | 2/2016 | Singer | ............... | G01N 33/18 702/6 |
| 2017/0044894 A1 * | 2/2017 | Surowinski | ............... | E21B 47/047 |
| 2017/0248501 A1 * | 8/2017 | Halden | ............... | G01N 33/1893 |
| 2019/0353630 A1 * | 11/2019 | Vepsäläinen | ............... | E21B 47/06 |

FOREIGN PATENT DOCUMENTS

| | | | | |
|---|---|---|---|---|
| CN | 112330927 A | * | 2/2021 | |
| CN | 109292056 B | * | 4/2021 | ............ B63C 11/34 |
| CN | 213337593 U | * | 6/2021 | |
| CN | 113334404 A | * | 9/2021 | |
| CN | 110864723 B | * | 1/2022 | ............ G01D 21/02 |
| CN | 215436872 U | * | 1/2022 | ............ B60F 3/0015 |
| CN | 113252735 B | * | 6/2022 | ............ G01D 21/02 |
| KR | 102118587 B1 | * | 6/2020 | |
| WO | WO-9829613 A1 | * | 7/1998 | ............ B09C 1/00 |

\* cited by examiner

COMPREHENSIVE SYSTEM FOR POTENTIAL RISK IDENTIFICATION AND POLLUTION PREWARNING OF GROUNDWATER

CROSS-REFERENCE TO THE RELATED APPLICATION

This application is based upon and claims priority to Chinese Patent Application No. 202210085529.2 filed on Jan. 25, 2022, the entire content of which is incorporated herein by reference.

TECHNICAL FIELD

The invention relates to the field of groundwater property monitoring, in particular to a comprehensive system for potential risk identification and pollution prewarning of groundwater.

BACKGROUND

At present, potential risk identification and pollution prewarning of groundwater are mainly realized by arranging measuring instruments underground, which are retrieved after a certain period of time, and then evaluation and analysis are conducted based on measured data, so that corresponding measures can be taken. According to this method, different measuring instruments can be adopted to measure water depth, liquid level, temperature, salinity, water quality and other parameters, and corresponding conclusions can be drawn according to measured data. However, this method has two serious defects: first, it can only measure a certain point, but cannot continuously monitor groundwater properties in a certain area, so it is impossible to get continuous monitoring data of this area and make comprehensive analysis; and second, because the instruments need to be kept underground until the right moment to retrieve, the data obtained are all delayed data, and information is not in real time, thus being not exactly the actual monitored content. To sum up, when potential risk identification and pollution prewarning of groundwater are conducted based on the data obtained by the existing method, the results are not consistent with the actual situation.

A technical means which can continuously monitor groundwater in a certain area is currently needed to make a more comprehensive and accurate judgment about groundwater in this area.

SUMMARY

The purpose of the invention is to overcome the above-mentioned defects in the prior art, and propose a comprehensive system for potential risk identification and pollution prewarning of groundwater, which realizes accurate layout of a monitoring cable and real-time continuous detection of groundwater properties in a certain area, so as to achieve potential risk identification and pollution prewarning of groundwater.

According to the technical scheme of the invention, a comprehensive system for potential risk identification and pollution prewarning of groundwater comprises a cable laying device, a monitoring cable and an electromagnetic retrieving device which are located in groundwater between two adjacent wells, wherein the two adjacent wells comprise a first well and a second well, the second well is located at a lower water level of the first well and communicates with the first well, the electromagnetic retrieving device is located in the second well, a plurality of sensors are arranged on the monitoring cable, and one end of the monitoring cable is connected to the cable laying device;

the cable laying device comprises a device body, an anchoring module and an electromagnetic adsorption module, the electromagnetic adsorption module is arranged on the device body, the anchoring module is arranged at a bottom of the device body, and the monitoring cable is connected to the cable laying device after passing through the anchoring module;

the anchoring module comprises a fixed pulley, a support pillar and an anchoring block, two ends of the fixed pulley are rotationally connected to an upper part of the support pillar, a bottom of the support pillar is fixedly connected to the anchoring block, a bottom of the anchoring block is provided with an anchor rod, the whole anchoring module can be fixedly inserted into the soil of groundwater, the monitoring cable is wound around the fixed pulley so that the monitoring cable is able to change from a vertical direction to a horizontal direction, and a horizontal end of the monitoring cable is connected to the cable laying device; and the electromagnetic retrieving device comprises a pull rod, a telescopic tube, a magnetic chuck and claws, the pull rod is located above the magnetic chuck and is connected to the magnetic chuck through the telescopic tube, a magnetic attraction force is generated between the magnetic chuck and the electromagnetic adsorption module, a plurality of claws are arranged at intervals in a circumferential direction of the magnetic chuck, protrusions are fixed to inner sides of the claws, and a size of a ring formed by the protrusions is smaller than that of the electromagnetic adsorption module.

In the invention, the cable laying device further comprises a device body, an underwater camera, an underwater lamp, a lifting propeller, a turboprop, a positioning module, an anchoring module and an electromagnetic adsorption module, the underwater camera, the underwater lamp, the lifting propeller, the turboprop, the positioning module, and the electromagnetic adsorption module are all arranged on the device body, and the anchoring module is arranged at a bottom of the device body.

The telescopic tube is made of a plastic material, so the telescopic tube is not only stretchable but also bendable. When the telescopic tube is stretched or bent, the magnetic chuck at the bottom of the telescopic tube moves up and down along with the telescopic tube or swings within 360°, thus ensuring that the magnetic chuck can be connected to the electromagnetic adsorption module accurately through adsorption.

An end, connected to the cable laying device, of the monitoring cable is sleeved with a caterpillar band, so as to ensure that the friction resistance generated by the cable laying device on the monitoring cable is reduced during the releasing or retrieving of the monitoring cable, preventing the monitoring cable from being damaged by friction in the laying process.

The invention has the following beneficial effects:

(1) In this system, the position and trajectory of the cable laying device can be accurately controlled, so that the monitoring cable can be accurately released by the cable laying device, and real-time continuous monitoring of groundwater properties in a certain area can be realized, thus forming a real-time and effective comprehensive system for potential risk identification and pollution prewarning of groundwater;

(2) The caterpillar band can ensure that the friction resistance generated by the cable laying device on the monitoring cable 3 is reduced during the releasing or retrieving of the monitoring cable, preventing the monitoring cable from being damaged by friction in the laying process; and (3) The electromagnetic retrieving device can not only ensure the reliable retrieval of the cable laying device, but also complete the laying of the monitoring cable.

Figure 1:
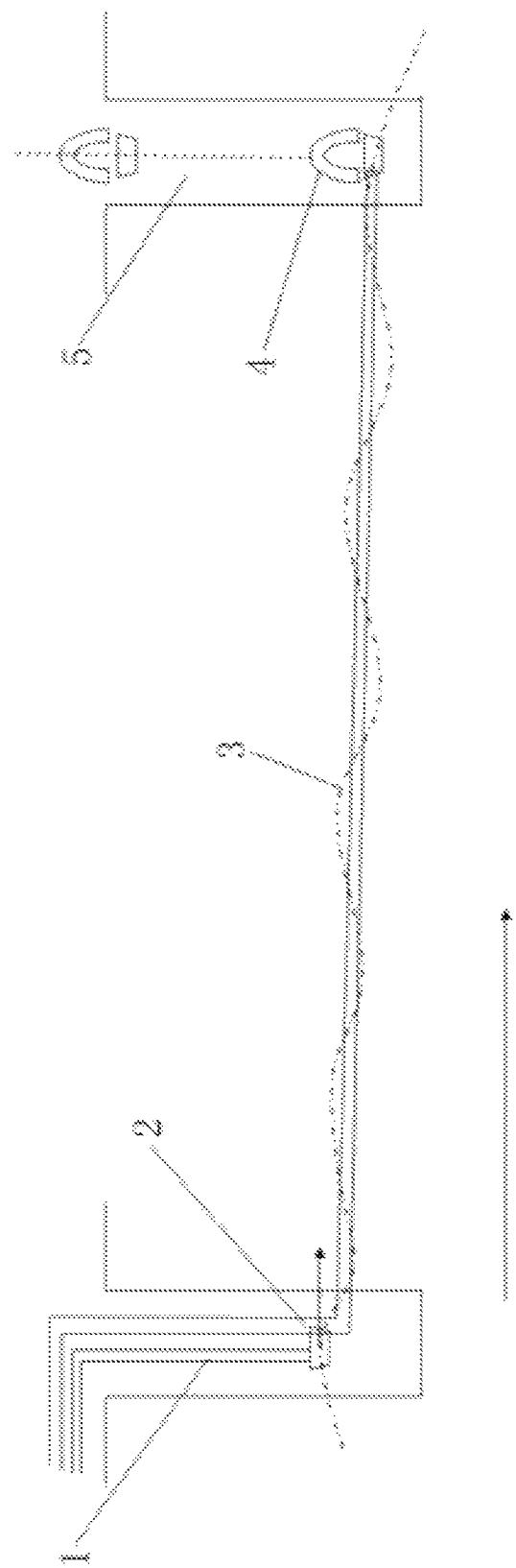
FIG. 1 is a connection structure diagram of the invention.

In the drawings: 1 first well; 2 cable laying device; 3 monitoring cable; 4 electromagnetic retrieving device; 5. second well; 6 underwater camera; 7 underwater lamp; 8 lifting propeller; 10 sensor; 11 caterpillar band; 12 turboprop; 13 positioning module; 14 anchoring module; 15 electromagnetic adsorption module; 16 fixed pulley; 17 support pillar; 18 anchoring block; 19 pull rod; 20 telescopic tube; 21 magnetic chuck; 22 protrusion; 23 claw.

DETAILED DESCRIPTION OF THE EMBODIMENTS

In order to make the above objects, features and advantages of the invention better understood, the specific embodiments of the invention will be described in detail below with reference to the accompanying drawings.

In the following description, specific details are set forth for the purpose of a full understanding of the invention. However, the invention can be implemented in many other ways different from those described here, and those skilled in the art can make similar extension without violating the connotation of the invention. Therefore, the invention is not limited by the specific embodiments disclosed below.

As shown in FIG. 1, a comprehensive system for potential risk identification and pollution prewarning of groundwater in the invention comprises a cable laying device 2, a monitoring cable 3 and an electromagnetic retrieving device 4 which are located in groundwater between two adjacent wells. In this embodiment, the two adjacent wells comprise a first well 1 and a second well 5, which may be wells that have been completed in advance for single-point monitoring, or wells that have been newly completed for measurement purposes. The first well 1 is located in an area with a high water potential, and the second well 5 is located at a lower water level of the first well 1 and communicates with the first well 1, so groundwater flowing through the first well 1 will flow to the second well 5. In the monitoring process, the first well 1 is taken as a place where the cable laying device starts working. The electromagnetic retrieving device is located in the second well 5.

In the first well 1, the cable laying device 2 is put into groundwater, and the cable laying device 2 will drift to the second well 5 along with the flow of the groundwater, during which the cable laying device 2 will drag the monitoring cable 3 forward continuously. The second well 5 is provided with the electromagnetic retrieving device. When the cable laying device 2 drifts to a place near the second well 5, the retrieval of the cable laying device 2 is realized by a magnetic force between the electromagnetic retrieving device and the cable laying device 2, and at the same time, an end of the monitoring cable 3 is retrieved too, thus completing the laying of the monitoring cable underground.

The monitoring cable 3 is an optical fiber cable, a plurality of sensors 10 are integrated on the monitoring cable 3, and the sensors 10 are connected to the monitoring cable 3 in parallel, so that monitoring data obtained by the sensors can be transmitted to a collection system through the monitoring cable 3 in real time, thereby achieving data acquisition and analysis.

Figure 2:
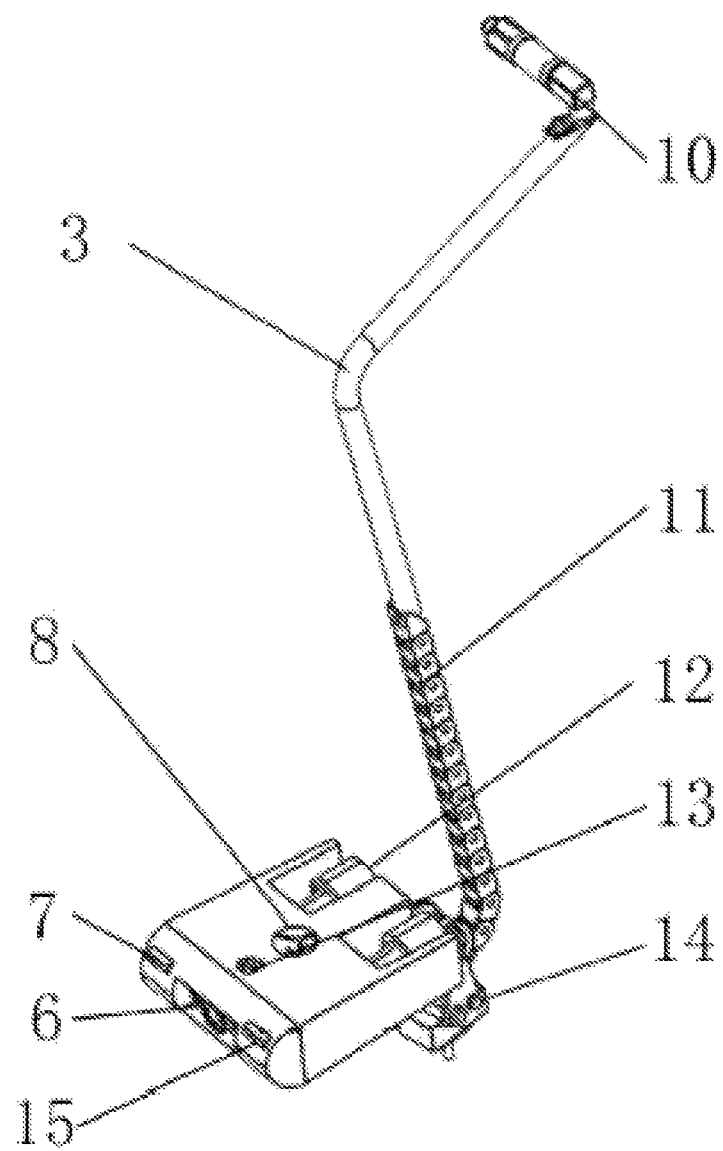
FIG. 2 is a structural diagram of a cable laying device.

As shown in FIG. 2, the cable laying device 2 comprises a device body, an underwater camera 6, an underwater lamp 7, a lifting propeller 8, a turboprop 12, a positioning module 13, an anchoring module 14 and an electromagnetic adsorption module 15, the underwater camera 6, the underwater lamp 7, the lifting propeller 8, the turboprop 12, the positioning module 13, and the electromagnetic adsorption module 15 are all arranged on the device body, and the anchoring module 14 is arranged at a bottom of the device body. The underwater camera 6 can conduct camera shooting underwater and transmit shooting materials through a cable, and an operator can perform corresponding operation through the camera shooting function. The underwater lamp 7 plays a lighting role underwater, providing guarantee for the use of the underwater camera 6. The lifting or lowering of the whole cable laying device 2 is realized by the lifting propeller 8. The turboprop 12 is used to realize forward and backward movement of an underwater vehicle and provide power for the cable laying device 2. The positioning module 13 is used to position the cable laying device to facilitate operation on the ground.

One end of the monitoring cable 3 is connected to the cable laying device 2, and an end, connected to the cable laying device 2, of the monitoring cable 3 is sleeved with a caterpillar band 11, so as to ensure that the friction resistance generated by the cable laying device 2 on the monitoring cable 3 is reduced during the releasing or retrieving of the monitoring cable, preventing the monitoring cable from being damaged by friction in the laying process.

Figure 3:
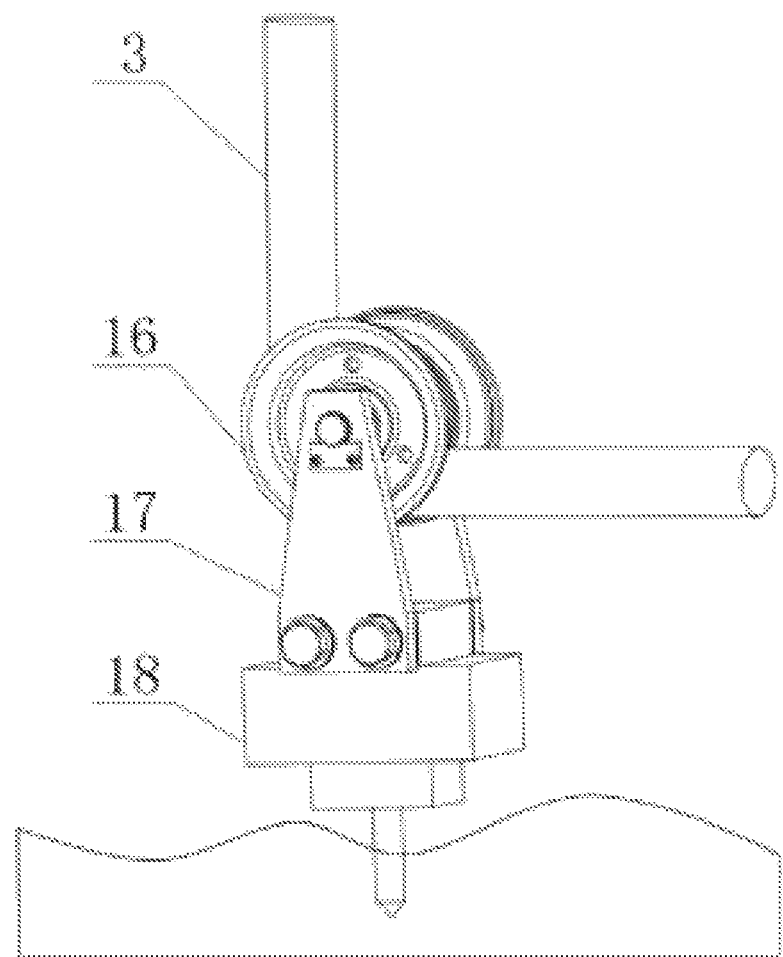
FIG. 3 is a structural diagram of an anchoring module.

After passing through the anchoring module 14, the monitoring cable 3 is connected to the cable laying device 2. As shown in FIG. 3, the anchoring module 14 comprises a fixed pulley 16, a support pillar 17 and an anchoring block 18, two ends of the fixed pulley 16 are rotationally connected to an upper part of the support pillar 17, a bottom of the support pillar 17 is fixedly connected to the anchoring block 18, a bottom of the anchoring block 18 is provided with an anchor rod, the whole anchoring module can be fixedly inserted into the soil of groundwater, the monitoring cable 3 is wound around the fixed pulley 16 so that the monitoring cable 3 is able to change from a vertical direction to a horizontal direction, and an end of the monitoring cable 3 is connected to the cable laying device 2 after becoming horizontal. When the cable laying device 2 is put into groundwater, the anchoring module 14 is released from the device body and fixedly inserted into the soil of groundwater. The anchoring module 14 turns the monitoring cable 3 from a vertical state to a horizontal state, and the horizontal end of the monitoring cable 3 is connected to the cable laying device 2. By arranging the anchoring module 14, the monitoring cable 3 can always be laid in a vertical state, which can not only reduce measurement blind corners as much as possible, but also prevent the monitoring cable 3 from being damaged in the laying process.

Figure 4:
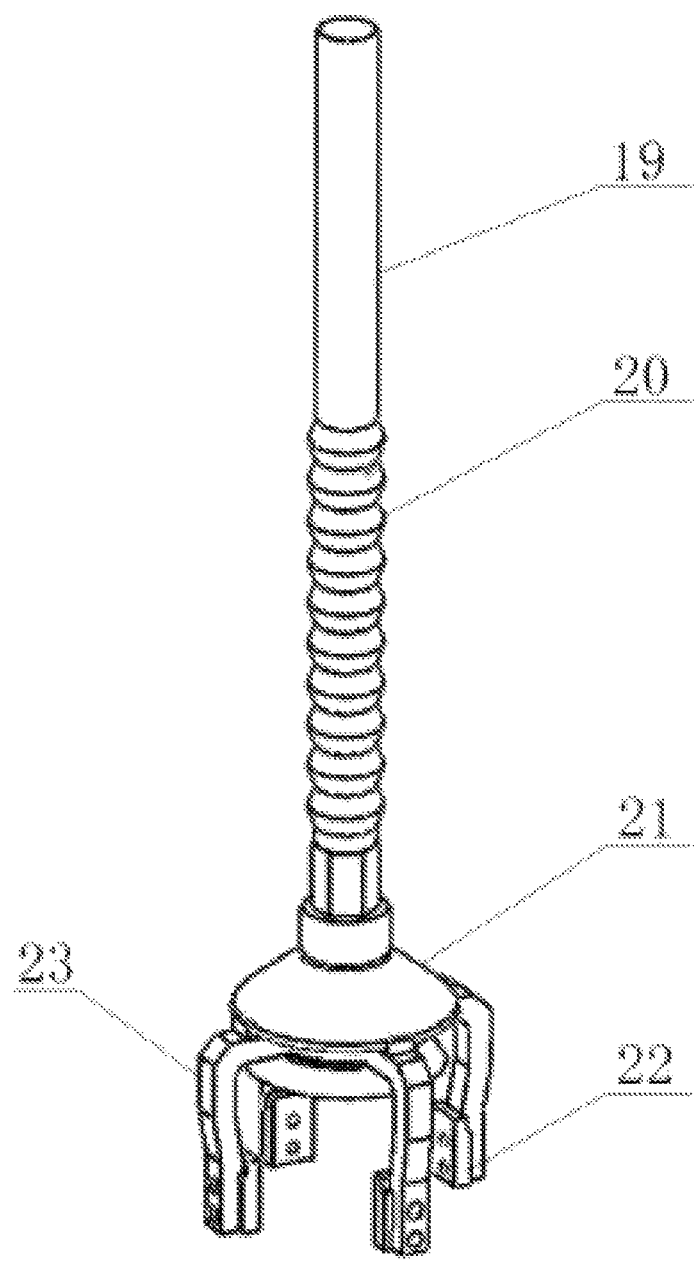
FIG. 4 is a structural diagram of an electromagnetic retrieving device.

When the monitoring cable 3 drifts to a place near the second well 5 with groundwater, the retrieval of the cable laying device 2 is realized by the electromagnetic retrieving device 4 in the second well and the electromagnetic adsorption module 15 on the cable laying device 2. In this embodiment, the electromagnetic adsorption module 15 is a waterproof electromagnet. As shown in FIG. 4, the electromagnetic retrieving device 4 comprises a pull rod 19, a telescopic tube 20, a magnetic chuck 21 and claws 23, the pull rod 19 is located above the magnetic chuck 21 and is connected to the magnetic chuck 21 through the telescopic tube 20, the magnetic chuck 21 can be lowered to the cable laying device 2 by means of the pull rod 19, and connection between the electromagnetic retrieving device 4 and the cable laying device 2 can be realized by a magnetic force generated between the magnetic chuck 21 and the electromagnetic adsorption module. The telescopic tube 20 is made of a plastic material, so the telescopic tube 20 is not only stretchable but also bendable. When the telescopic tube is stretched or bent, the magnetic chuck 21 at the bottom of the telescopic tube moves up and down along with the telescopic tube or swings within 360°, thus ensuring that the magnetic chuck 21 can be connected to the electromagnetic adsorption module accurately through adsorption. A plurality of claws 23 are arranged at intervals in a circumferential direction of the magnetic chuck, protrusions 22 are fixed to inner sides of the claws 23, and a size of a ring formed by the protrusions 22 is smaller than that of the electromagnetic adsorption module. In the adsorption connection process between the magnetic chuck 21 and the electromagnetic adsorption module, the magnetic force between the magnetic chuck 21 and the electromagnetic adsorption module enables the magnetic chuck 21 to overcome the resistance generated by the protrusions 22 on the electromagnetic adsorption module to snap-fit into the claws 23, and then make the electromagnetic adsorption module snap-fit into the claws 23 under the limiting effect of the protrusions 22. At this point, under the dual action of an adsorption force between the electromagnetic chuck and the electromagnetic adsorption module, and the clamping force of the claws and the protrusions, firm connection between the electromagnetic retrieving device and the electromagnetic adsorption module is realized, and falling off of the cable laying device caused by the gravity of the cable laying device or the resistance of groundwater flow in the retrieval process of the cable laying device is prevented. When the electromagnetic chuck and the electromagnetic adsorption module are firmly connected, the cable laying device is lifted out of the second well 2 by means of the pull rod 19, thus realizing the retrieval of the cable laying device.

The working process of the system is as follows. At first, two or more wells should be selected according to various factors such as groundwater flow direction. After the wells are selected, the cable laying device 2 is placed in the first well 1. The cable laying device 2 carries the monitoring cable 3 which is provided with a certain number of sensors 10. Data measured by the sensors can be transmitted in real time through the monitoring cable 3. When the cable laying device 2 is located in groundwater, an operator can accurately analyze the position of the cable laying device according to the underwater camera 6 and the positioning module 13, and then control the position of the cable laying device by means of the lifting propeller 8 and the turboprop 12. The electromagnetic retrieving device 4 is placed in groundwater and waits for the approach of the cable laying device 2. In the process of approaching, the electromagnetic adsorption module 15 is tightly butted with the electromagnetic retrieving device 4 to form an integral body. At this point, the cable laying device is firmly connected to a bottom of the electromagnetic retrieving device 4, and is lifted and retrieved. The electromagnetic retrieving device 4 ascends with the cable laying device 2, and the monitoring cable 3 also ascends because it is attached to the cable laying device 2, so that the retrieval of the cable laying device 2 and the laying of the monitoring cable 3 are completed. Working data monitored by the sensors on the monitoring cable 3 can be transmitted in real time through the monitoring cable, so that parameters can be monitored in real time. In this way, the real-time property and continuity of data can be ensured, and real-time continuous monitoring of groundwater situation in a certain watershed of this area can be completed. Through joint inversion of the monitored data, the change mechanism of some related parameters can be obtained, so as to achieve potential risk identification and pollution prewarning of groundwater, and thus a real-time and effective comprehensive system for potential risk identification and pollution prewarning of groundwater is formed.

The comprehensive system for potential risk identification and pollution prewarning of groundwater provided by the invention has been introduced in detail above. In this article, specific examples are used to explain the principle and implementation of the invention, and the description of the above embodiments is only used to help understand the method of the invention and its core ideas. It should be pointed out that for those of ordinary skill in the art, multiple improvements and modifications may be made to the invention without departing from the principle of the invention, and these improvements and modifications also fall within the scope of protection of the claims of the invention. The above description of the disclosed embodiments enables those skilled in the art to implement or use the invention. Various modifications to these embodiments will be apparent to those skilled in the art, and the general principles defined herein may be implemented in other embodiments without departing from the spirit or scope of the invention. Therefore, the invention should not be limited to the embodiments shown herein, but should accord with the widest scope consistent with the principles and novel features disclosed herein.

What is claimed is:

1. A comprehensive system for potential risk identification and pollution prewarning of groundwater, comprising a cable laying device, a monitoring cable, and an electromagnetic retrieving device which are located in groundwater between two adjacent wells, wherein the two adjacent wells comprise a first well and a second well, the second well is located at a lower water level of the first well and communicates with the first well, the electromagnetic retrieving device is located in the second well, a plurality of sensors are arranged on the monitoring cable, and one end of the monitoring cable is connected to the cable laying device;

the cable laying device comprises a device body, an anchoring module and an electromagnetic adsorption module, the electromagnetic adsorption module is arranged on the device body, the anchoring module is arranged at a bottom of the device body, and the monitoring cable is connected to the cable laying device after passing through the anchoring module;

the anchoring module comprises a fixed pulley, a support pillar, and an anchoring block, two ends of the fixed pulley are rotationally connected to an upper part of the support pillar, a bottom of the support pillar is fixedly connected to the anchoring block, a bottom of the anchoring block is provided with an anchor rod, the monitoring cable is wound around the fixed pulley allowing the monitoring cable to change from a vertical direction to a horizontal direction, and a horizontal end of the monitoring cable is connected to the cable laying device; and the electromagnetic retrieving device comprises a pull rod, a telescopic tube, a magnetic chuck, and a plurality of claws, the pull rod is located above the magnetic chuck and is connected to the magnetic chuck through the telescopic tube, a magnetic attraction force is generated between the magnetic chuck and the electromagnetic adsorption module, the plurality of claws are arranged at intervals in a circumferential direction of the magnetic chuck, protrusions are fixed to inner sides of the plurality of claws, and a size of a ring formed by the protrusions is smaller than that of the electromagnetic adsorption module.

2. The comprehensive system for potential risk identification and pollution prewarning of groundwater according to claim 1, wherein the cable laying device further comprises a device body, an underwater camera, an underwater lamp, a lifting propeller, a turboprop, a positioning module, an anchoring module, and an electromagnetic adsorption module, wherein the underwater camera, the underwater lamp, the lifting propeller, the turboprop, the positioning module, and the electromagnetic adsorption module are all arranged on the device body, and the anchoring module is arranged at a bottom of the device body.

3. The comprehensive system for potential risk identification and pollution prewarning of groundwater according to claim 1, wherein the telescopic tube is made of a plastic material.

4. The comprehensive system for potential risk identification and pollution prewarning of groundwater according to claim 1, wherein an end, connected to the cable laying device, of the monitoring cable is sleeved with a caterpillar band.

* * * * *